Figure 1:
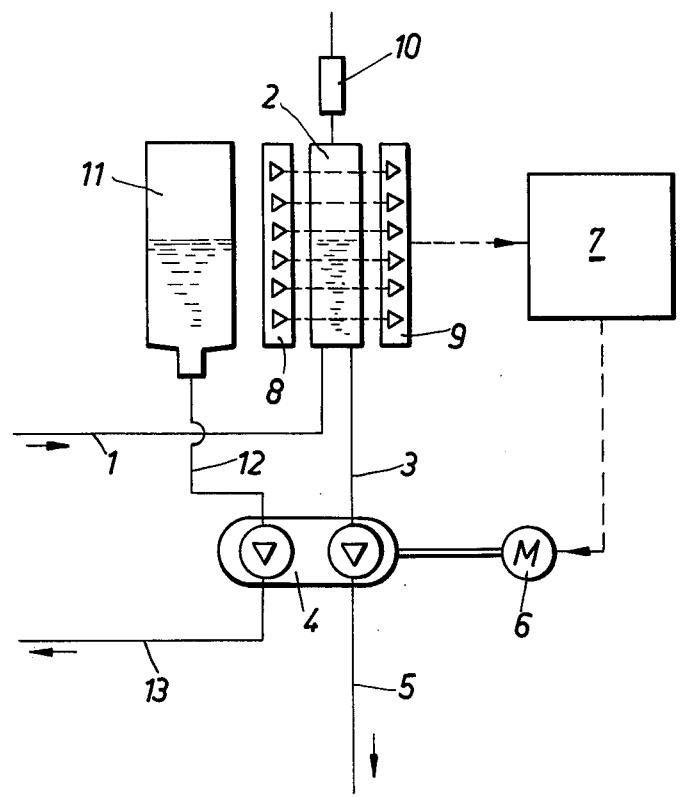

United States Patent [19]

Schael

[11] 4,275,726
[45] Jun. 30, 1981

[54] APPARATUS FOR FLUID BALANCING UNDER STERILE CONDITIONS

[75] Inventor: Wilfried Schael, Bad Homburg, Fed. Rep. of Germany

[73] Assignee: Dr. Eduard Fresenius, Chemisch-pharmazeutische Industrie KG Apparatebau KG, Bad Homburg, Fed. Rep. of Germany

[21] Appl. No.: 966,497

[22] Filed: Dec. 4, 1978

[30] Foreign Application Priority Data

Dec. 9, 1977 [DE] Fed. Rep. of Germany ....... 2754894

[51] Int. Cl.$^2$ .............................................. A61J 7/00
[52] U.S. Cl. .............................. 128/213 A; 128/214 E
[58] Field of Search ...................... 128/213; 417/477; 210/321 A, 321 B

[56] References Cited

U.S. PATENT DOCUMENTS

| 3,520,298 | 7/1970 | Lange | 128/213 A |
| 3,709,222 | 1/1973 | De Vries | 128/213 A |
| 4,096,859 | 6/1978 | Agarwal et al. | 128/213 A |
| 4,108,575 | 8/1978 | Schäl | 417/477 |
| 4,190,047 | 2/1980 | Jacobsen et al. | 128/213 A |

FOREIGN PATENT DOCUMENTS 2535650  2/1977  Fed. Rep. of Germany ........... 417/477

Primary Examiner—Kyle L. Howell
Assistant Examiner—T. J. Wallen
Attorney, Agent, or Firm—W. G. Fasse; D. F. Gould

[57] ABSTRACT

Apparatus for removing fluid from and supplying fluid to the human body in substantially equal quantities includes a double tube pump (1), a measuring chamber (2), and a supply container (4), the pump being arranged to deliver fluid from the supply container to the body by a line (13) while removing fluid at an equal rate from the measuring chamber, which receives fluid from the body by a line (1). The measuring chamber is provided with sensing means (8,9) which supply signals in response to variations in the level of fluid in the measuring chamber to a controller (7) which controls the pump motor speed. For use in diuresis and haemofiltration, an additional single pump (14) in a discharge line (16) from the measuring chamber is controllable by a device (18) to remove excess fluid from the measuring chamber. The double pump is the same as that described in U.S. Pat. No. 4,108,575.

10 Claims, 6 Drawing Figures

APPARATUS FOR FLUID BALANCING UNDER STERILE CONDITIONS

BACKGROUND OF THE INVENTION

The invention relates to apparatus for bringing into harmony two flows of fluid and the amounts of fluid which result from such flows over a predetermined period of time, or for achieving a given difference between the two flows or quantities of fluid, under sterile conditions, that is to say, avoiding germ infection or other contamination of the fluids. Such an apparatus can be used with advantage inter alia in certain medicinal treatment processes, if the fluid which is drawn from one patient is to be continuously replaced by another fluid to the same degree or with a defined difference between the two amounts of fluid.

An example of a process of this kind is exchange blood transfusion in which blood is taken from the patient and replaced by blood from an outside source. In order to avoid inadmissible fluctuations in the total volume of blood in the circulation of the patient, during this process, the amounts of blood drawn from and supplied to the patient must be as closely parallel to each other as possible.

A second example is infusion therapy in conjunction with forced diuresis, which is used for example in certain cases of poisoning in order to remove the poison from the body as quickly as possible by increased urine excretion which is triggered off by medicament means. In this case, it is necessary for the high loss of fluid to be replaced as regularly as possible, for which purpose the intravenous infusion of suitable amounts of fluid is frequently employed. The infused fluid must be matched in regard to its quantity to the quantity of urine which is excreted.

A third example is haemofiltration (also called haemodiafiltration) in which a filtrate is sucked out of the blood of the patient through a filter, the filtrate substantially comprising water and low-molecular blood constituents, including also urine-related substances which would normally have to be excreted by way of the kidneys. This process is used in particular for replacing a failing kidney function. The major part of the fluid drawn off must be replaced by intravenous infusion of a substitution solution, in parallel with the withdrawal of the filtrate.

The above-listed examples always involve the problem of introducing a substitute fluid (blood or infusion solution) into the patient's circulation, in accordance with the withdrawal or automatic excretion of another fluid (blood, urine, filtrate). The supply of substitute fluid must obviously be effected under absolutely sterile conditions. The latter requirement severely limits the technical means which can be employed, and means that the sterile substitute fluid must be supplied to the patient from a sterile container through a sterile tube and possibly further sterile connecting and communicating members. For reasons of safety and operating simplification, it is nowadays generally usual for the members which are employed for such purposes to be in the form of single-use articles which are supplied in a sterile condition by the manufacturer and are thrown away when they have been used once.

Balancing, that is to say, achieving a condition of harmony between the amounts of fluid which are supplied and withdrawn, possibly taking into account an intentional difference between the two amounts of fluid, is effected in many cases by observation and manual control of the process, for example by the fluid which is withdrawn being collected in a calibrated vessel and the supply of substitute fluid being regulated in accordance with the values which are read off on the calibrated vessel. This process which requires continuous observation is very labour-intensive. Disadvantageous consequences can result for the patient, due to errors in reading off the values or due to other human error.

The present invention is therefore based on the problem of providing a process and apparatus with the aim of automating balancing operations of the kind set out above, and thereby facilitating the work of the doctor and the medical staff and achieving a higher degree of safety for the patient.

In the past, it has already been usual to convey fluids under sterile conditions by using hose or tube pumps, preferably of the so-called roller pump type, as in this kind of pump the conveyor medium only comes into contact with the pump tube, which is particularly easy and cheap to produce as a sterile article intended to be used only once. However, these pumps are not readily suitable for precise control of quantities of fluid. Important factors for this purpose are inter alia the tolerances in respect of the internal diameter of the tube and thus the internal cross-sectional area of the tube. Even when the tubes are produced particularly carefully, according to manufacturers' information, the diameter tolerances are of the order of from 2 to 3% with the usual extrusion method, so that the cross-sectional area and thus the amount delivered per unit of time already suffers from a deviation of the order of from 4 to 6%. Further deviations can result from the fact that the tube cannot be fitted into the pump head in a manner which can be precisely reproduced, for example because the tube is twisted or installed with a different pre-stressing. A further reason for an inaccurate metering operation is the fatigue from which the tube material suffers in the passage of time and which results in the tube no longer returning completely to its original shape after it has been relieved of load. This therefore results in a reduction in the internal cross-sectional area and a fall in pumping output. Finally, the pressure obtaining at the input, on the suction side of the pump, should be mentioned as a particularly serious influence. Irrespective of the resilient properties of the tube, there will be a different degree of filling of the tube, which will thus influence the pump output, when the pressure at the pump input varies. This effect can assume considerable proportions particularly when the input pressure of the pump is below atmospheric pressure.

The factors listed above make it seem at first sight as though there is not a great deal of prospect for success in using tube pumps for the desired fluid balancing action, in view of the requirement that the balancing error should if possible not be more than 0.5% for example in a haemofiltration process. However, while using tube pumps, the invention provides steps whereby the fluid balancing error is readily reduced to the required degree and is even reduced to a substantially greater degree.

SUMMARY OF THE INVENTION

According to the invention there is provided an apparatus for balancing fluids drawn from a patient and returned back into the patient, for example, in connection with an exchange blood transfusion or in connection with a diuresis, or a haemofiltration, or a heamodiafiltration treatment. For this purpose a measuring chamber and a container for the fluid such as blood or the like are operatively interconnected with a double tube pump operative in the discharge line from the measuring chamber and in the supply line from the container to the patient. A filling level measuring device controls the motor for the double tube pump so that the speed of rotation of the double tube pump depends on the fluid quantity measured.

BRIEF FIGURE DESCRIPTION

Figure 2:
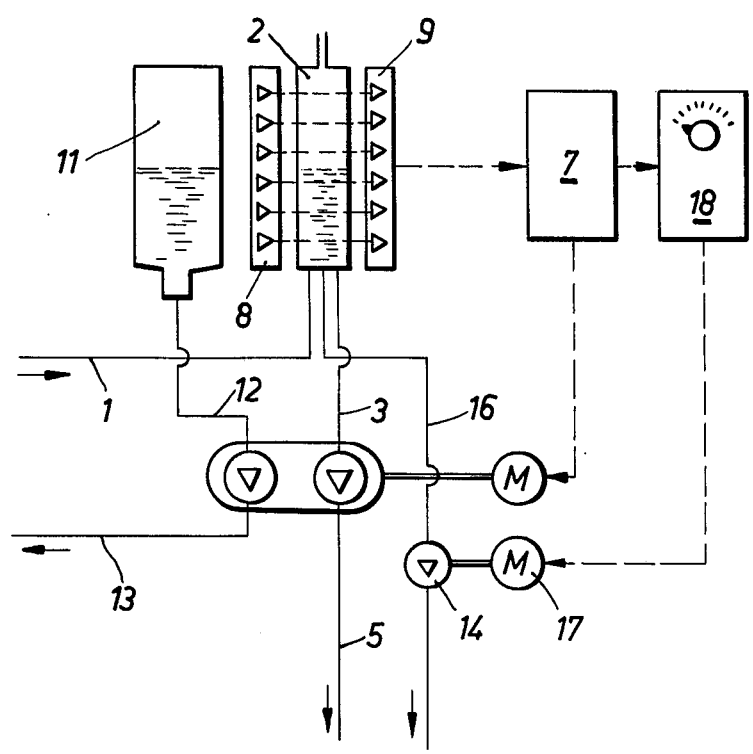
Figure 3:
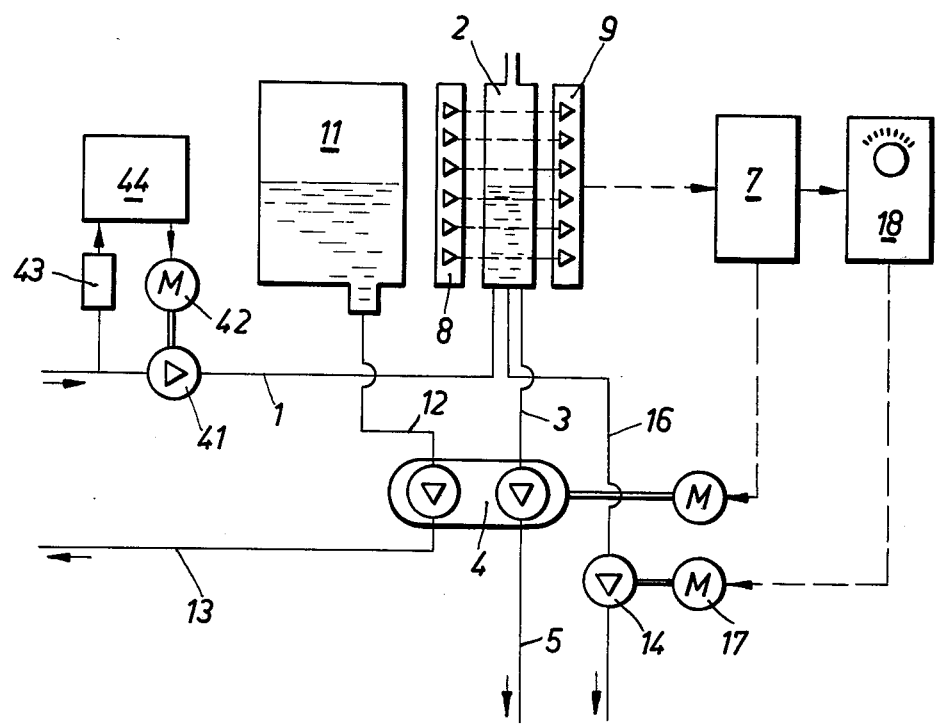
Figure 4:
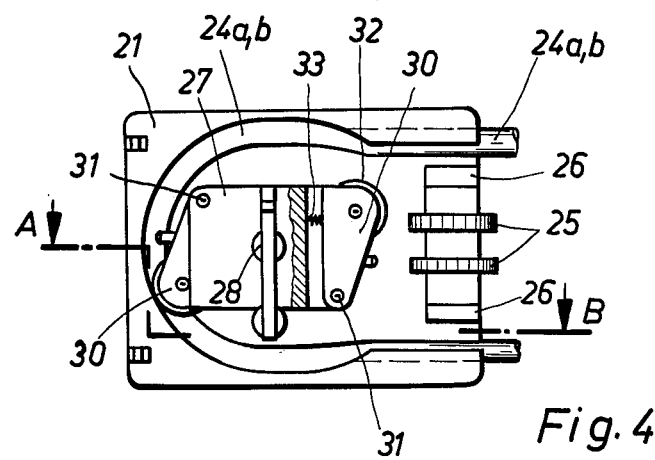
Figure 5:
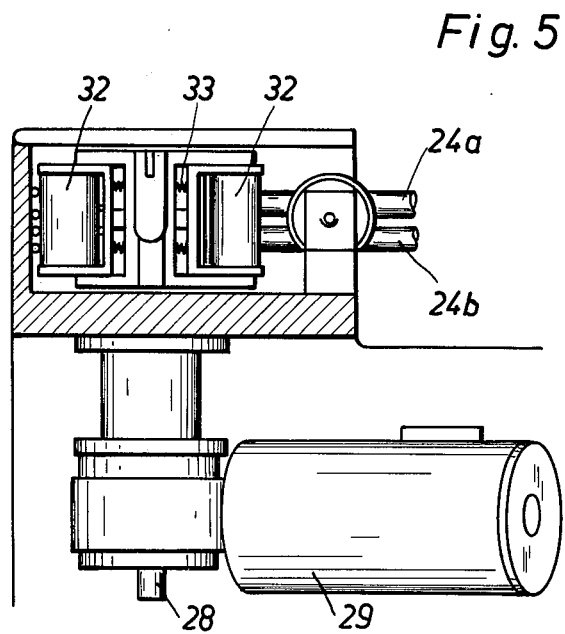
Figure 6:
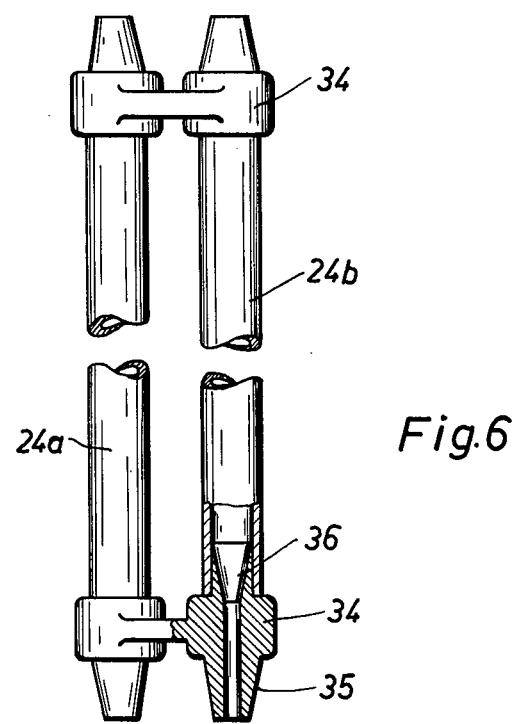

The invention is described hereinafter in the form of examples with reference to the drawings, in which:

FIG. 1 shows a diagrammatic view of a balancing apparatus for exchange blood transfusions, FIG. 2 shows apparatus for volume balancing in forced diuresis, FIG. 3 shows a balancing apparatus for haemofiltration, FIG. 4 shows a plan view on to the pump head of the double tube pump, FIG. 5 shows a view in section taken along line A–B in FIG. 4, and FIG. 6 shows a pre-fabricated double pump tube unit.

DETAILED DESCRIPTION OF PREFERRED EXAMPLE EMBODIMENTS AND OF THE BEST MODE OF THE INVENTION

In the case of the apparatus shown in FIG. 1, the blood which is drawn from the patient is passed by way of the tube 1 to a measuring chamber 2 and from there passes through the tube 3 to one half of a double tube pump 4 and thereafter flows through the tube 5 into a collecting vessel (not shown) or the like. The electrical drive motor 6 for the double tube pump 4 is controlled by way of an electronic controller 7. The object of this controller is to set the drive speed of the double tube pump in such a way that the level to which the measuring chamber 2 is filled remains substantially constant and thus an amount of fluid is pumped out of the measuring chamber by the tube pump through the tube 3, which is the same as the amount of fluid which is introduced into the measuring chamber 2 by way of the line 1. For this purpose, a means for measuring the level of filling of the measuring chamber is provided thereon. Various known means can be considered for this purpose, being mainly those means which permit the level of filling to be measured from the exterior, without contact with the contents of the measuring chamber. Such means are for example capacitive filling level measuring means having electrodes which are applied to the exterior of the measuring chamber or filling level measuring means which operate in accordance with the transmission process using light or ultra-sound. In FIG. 1, the latter measuring principle is indicated by way of example by a row of radiation transmitters 8 and radiation receivers 9. Information concerning the level of filling of the measuring chamber can be converted by known technical means for example into an electrical voltage which corresponds to the level of filling of the measuring chamber. This actual voltage is compared in the controller 7 to a desired voltage which corresponds to a predetermined desired level of filling. As long as the actual voltage is lower than the desired voltage, and accordingly the actual level to which the measuring chamber is filled is lower than the desired level, no drive power is fed to the motor 6. However, the motor receives an increasing drive power from the controller, in proportion as the actual level to which the measuring chamber is filled exceeds the desired level, in order in this way to stabilise the actual level of filling in the vicinity of the desired level. There are many different designs of controllers which can supply a motor with electrical power which rises with increasing difference, on the basis of comparison between an actual value and a desired value.

The measuring chamber 2 is either open upwardly or, if necessary, is vented by way of a sterile filter 10 which is non-transmissive in respect of bacteria, so that in any case atmospheric pressure obtains in the measuring chamber. Under the above-stated conditions, a virtually constant pressure obtains at the input of the tube pump, which pressure is equal to atmospheric pressure, if the hydrostatic pressure drop and the pressure loss caused by flow are neglected. This, and automatic adaptation of the pumping output to the supply flow of fluid by way of the line 1, is the actual aim of the combination of measuring chamber, level measuring means and controller.

The other half of the double tube pump 4 is used to feed the patient with the substitute fluid, in the present example blood from a blood plasma. For this purpose, the supply container 11 which is vented by way of a sterile filter or which is in the form of a collapsible bag is connected to the input of this part of the pump by way of the tube 12, and a tube 13 leads from the output of the pump to the patient. Because the supply container 11 is suspended approximately at the level of the measuring chamber 2, virtually the same pressure obtains at the input of this half of the pump, as at the input of the other half of the pump. Bringing the input pressures into harmony in this way fulfils an essential pre-requisite for achieving the desired equality between the conveyor flows in the lines 1 and 13. In addition, because of the envisaged use of identical pump tubes of identical material, the fatigue effect is equal in both halves of the pump, so that no differences are to be expected to result from this factor. A similar consideration also applies for the drive conditions which are the same for both halves of the pump, by virtue of the common drive.

FIGS. 4 and 5 show an advantageous construction of the double tube pump. The pump head comprises a stator 21 and a rotor 27. When the two pump tubes 24a and 24b are fitted into the stator, they are bent through 180° and fit closely against the inward surface of the stator. Clamp members 26 which can be actuated by knurled nuts 25, for fixing the tubes 24a and 24b in the stator 21, are arranged at the open side of the stator. FIG. 4 shows the clamp members before the ends of the tubes are clamped fast.

Arranged in the middle of the stator is the rotor 27 which can be rotated by way of its shaft 28 by a geared motor 29. Two identical levers 30 are fixed on the rotor, each being pivotal about a respective axis 31. The levers each carry a respective roller 32 which is mounted rotatably about its axis and which rolls against the pump tubes which are fitted in the stator, when the rotor is rotated, so that the tubes are compressed against the inward surface of the stator at the point at which they are subjected to pressure by the rollers, to such an extent that the tube cross-section is closed at that point and the rollers push the contents of the tubes in front of them, by virtue of their rolling movement against the tubes.

Each of the levers 30 is urged radially outwardly by two pre-stressed coil springs 33, the maximum deflection movement of the levers being limited by a stop. The rollers 32 are resiliently adapted to the wall thickness of the tubes, by virtue of the action of the springs. Suitable selection of the spring force makes it possible for the tubes used to be reliably clamped closed at the point at which they are subjected to pressure by the rollers while however avoiding overloading the tube material.

The pump described above by way of example appears particularly suitable for the present purpose, but other equivalent tube pump constructions which provide for reliably clamping closed the tubes, without overloading the tube material, can also be used.

An important factor in regard to a small difference in the conveyor output of the two halves of the pump is that the two pump tubes should be as close to each other as possible in respect of their dimensions and the properties of their materials. In addition, it is desirable for the two tubes to be fitted into the pump head in as closely defined and as regular a manner as possible. In embodying the concept of the invention therefore, in consideration of these points, it is provided that the two pump tubes may be used in the form of a prefabricated unit, as is shown in a simplified form by way of example in FIG. 6. Such a unit comprises two tube portions 24a and 24b which are of equal length and which are cut off one directly after the other from the tube material. Thus, it can be assumed that, by virtue of the conditions of manufacture being identical, the two tubes are precisely identical in regard to their dimensions and the properties of their materials. The two tubes are joined to two end members 34, while avoiding any twisting, for example by adhesive or by other conventional connecting methods. The end members have for example tapered connection nozzles 35 in order to form the connections with the remainder of the tube system. Even if a prefabricated unit of this kind is handled with less care, the unit ensures that the two tubes are fitted into the pump head in a highly regular manner as the end members permit neither different longitudinal extension nor twisting of the tubes. Using the features listed above makes it possible for the balancing error between the two flows of fluid which are to be brought into harmony, to be kept at a very low level. Measurements on a system of this kind have shown that the differences under routine conditions can typically be of the order of from 0.2 to 0.5%, thus giving a safety factor which is ten times better than the limit which is usually considered permissible for example for haemofiltration treatment.

The remainder of the technical arrangement of the system shown in FIG. 1 does not have any peculiarities and can be varied to meet particular requirements. For example, the measuring chamber can be in the form of a relatively thin tube in order to provide a small dead volume and to cause the level measuring means to have a sensitive response. It is also possible for example for the supply of fluid into the measuring chamber to be from above, so as to permit the flow of fluid to be observed. It may also be advantageous for the supply container 11 or the line 12 to be monitored with a suitable sensor, for example a light barrier arrangement or an ultrasonic barrier arrangement, in order to detect when the supply container is emptying, to automatically interrupt the transfusion by suitable means, and to trigger off a warning signal.

A further example of apparatus according to the invention is the system which is diagrammatically shown in FIG. 2, for automatic balancing in forced diuresis. In this case the medium which flows into the system through the line 1 is urine which is drained from the urine bladder of the patient by way of a catheter. At the same time, an infusion solution is fed to the patient by way of the line 13. It may be desirable to include a buffer or surge vessel (not shown in FIG. 5) in the line 13.

The system diagrammatically shown in FIG. 2 also differs from that shown in FIG. 1 in that it includes an additional pump 14 which pumps fluid from the measuring chamber 2 by way of the line 16. This is provided in order to branch off a given proportion of the urine before the balancing operation so that the quantity of infusion solution which is fed to the patient is correspondingly less than the amount of urine which is drawn off, depending on the amount of fluid which the patient receives from other sources. The drive motor 17 of the additional pump is controlled by means of a control device 18 at which the amount of fluid which is to be tapped off can be set. As the degree of accuracy in regard to determining the volume of the amount of fluid which is tapped off is not subject to extreme requirements, the pump 14 may be for example a normal tube pump, and measurement of the volume which is conveyed by the pump 14 may be effected with a sufficient degree of accuracy by counting the number of revolutions of the drive motor 17.

A third example of apparatus according to the invention is the apparatus which is shown in diagrammatic form in FIG. 3, for balancing in haemofiltration. The fluid which in this case flows into the measuring chamber 2 by way of the line 1 is the filtrate which is obtained in known manner from the blood of the patient. For filtration purposes, it is normally necessary to produce a given reduced pressure on the outlet side of the filter. This purpose is served by the pump 41 with its drive motor 42 in conjunction with the pressure measuring transducer 43 and the controller 44. The drive motor of the pump is controlled by the controller 44 in such a way that the reduced pressure as measured on the suction side of the pump with the pressure measuring transducer 43 reaches a predetermined desired value.

As in the previous example, a part of the filtrate which is passed into the measuring chamber 2 is tapped off by way of the line 16 and the pump 14, in order to provide a given pre-set net withdrawal of fluid. The remainder of the filtrate passes through the line 3, the right-hand half of the pump 4 and the line 5, for example into a collecting container (not shown). By virtue of the above-described properties of the balancing system, an equal amount of substitution solution is drawn from the supply container and fed to the extra-corporal blood circulation of the patient by the left-hand half of the double tube pump 4 and the line 13.

Although the invention has been described with reference to specific example embodiments, it will be appreciated, that it is intended, to cover all modifications and equivalents within the scope of the appended claims.

What is claimed is:

1. An apparatus for balancing the fluids withdrawn from a patient and the fluids simultaneously returned into the patient, comprising first pump means having a pump inlet and a pump outlet, measuring chamber means (2) for measuring a quantity of fluid withdrawn from the patient by said pump means, first conduit means (1) operatively connecting an inlet of said measuring chamber means (2) to a patient for withdrawing fluid from the patient into the measuring chamber means, second conduit means (3) operatively connecting an outlet of said measuring chamber means to said pump inlet for withdrawing fluid from the measuring chamber means, third conduit means (5) connected to said pump outlet to discharge fluid, supply container means (11), second pump means also having respective pump inlet means and respective pump outlet means, fourth conduit means (12) operatively connecting said supply container means (11) to said pump inlet means of said second pump means and fifth conduit means (13) operatively connecting said pump outlet means of said second pump means to a patient for returning fluid into a patient, first motor means (6) operatively connected to said first and second pump means for driving said first and second pump means in unison, said conduit means comprising respective conduit sections operatively arranged for pumping fluid therethrough in unison by said first and second pump means, and control means (7, 8, 9) operatively responsive to the rise and fall of the filling level in said measuring chamber means (2) and operatively connected to said first motor means (6) for controlling the speed of operation of said first and second pump means in response to the filling level in said measuring chamber means, whereby the fluid withdrawal and fluid return take place simultaneously while the withdrawal rate and the return rate are continuously balanced relative to each other during treatment so that withdrawing excessive liquid quantities from the patient is prevented.

2. The apparatus of claim 1, wherein said measuring chamber means and said supply container means are adapted to hold blood for a blood transfusion.

3. The apparatus of claim 1, wherein said measuring chamber means is adapted to hold urine and wherein said supply container means is adapted to hold an infusion solution for a forced diuresis treatment, said apparatus further comprising sixth conduit means (16) operatively connected to said measuring chamber means, third pump means (14) operatively connected to said sixth conduit means, second motor means (17) connected for driving said third pump means and adjustment means (18) operatively connected to said control means (7) and to said second motor means for controlling the speed of operation of said third pump means to adjust the amount of fluid which is to be tapped off from said measuring chamber means through said sixth conduit means prior to any balancing operation.

4. The apparatus of claim 3, wherein said first, second, and third pump means comprise each a hose pump.

5. The apparatus of claim 1, wherein said measuring chamber means is adapted to hold filtrate and wherein said supply container means is adapted to hold a substitute solution for a hemofiltration or for a hemodiafiltration treatment, wherein said first conduit means comprise a filtrate conduit section (1) operatively connected to said measuring chamber means, said apparatus further comprising sixth conduit means (16) operatively connected to said measuring chamber means, third pump means (14) operatively connected to said sixth conduit means, second motor means (17) connected for driving said third pump means, adjustment means (18) operatively connected to said control means (7) and to said second motor means for controlling the speed of operation of said third pump means to adjust the amount of filtrate to be tapped off from said measuring chamber through said sixth conduit means prior to any balancing operation, fourth pump means (41) operatively connected into said filtrate conduit section (1), third motor means (42) operatively connected to said fourth pump means (41), pressure sensor means (43) operatively connected to said filtrate conduit section (1), further control means (44) operatively responsive to said pressure sensor means (43) and operatively connected to said third motor means (42) for operating said fourth pump means (41) in response to said pressure sensor means.

6. The apparatus of claim 5, wherein said first, second third and fourth pump means are hose pump means.

7. The apparatus of claim 5, wherein said pressure sensor means are operatively connected to said filtrate conduit section upstream of said fourth pump means.

8. The apparatus of claim 1, wherein said first pump means comprise hose pump means including pump head means, said respective conduit sections comprising hose members ganged to be driven in unison by said pump head means.

9. The apparatus of claim 8, wherein said pump head means comprise a stator and a rotor including two outwardly pivotable spring loaded rotor pressure rollers, said stator including a semi-circular, inwardly facing surface for supporting said hose members in ganged relationship for engagement by said rotor pressure rollers, and axially displaceable clamp members including threaded means for securing said hose sections in the stator.

10. The apparatus of claim 9, wherein said hose members are made of the same material and have the same length, diameter, wall thickness, and elasticity, each hose member further comprising at each end thereof connecting nipple means (34) including oppositely extending socket means (35, 36), and bridging means operatively interconnecting the nipple means in pairs in a side-by-side relationship to form one nipple pair at each end of said hose members.

* * * * *